United States Patent [19]

Marquez et al.

[11] 4,275,057
[45] Jun. 23, 1981

[54] SEVEN-MEMBERED RING COMPOUNDS AS INHIBITORS OF CYTIDINE DEAMINASE

[75] Inventors: Victor E. Marquez, Gaithersburg; Paul S. Liu, Kensington; John S. Driscoll, Rockville, all of Md.

[73] Assignee: The United States of America as represented by the Department of Health, Education and Welfare, Washington, D.C.

[21] Appl. No.: 115,900

[22] Filed: Jan. 28, 1980

[51] Int. Cl.³ .................... A61K 31/70; C07H 17/02; C07H 19/04
[52] U.S. Cl. .................... 424/180; 536/23; 536/29; 435/184
[58] Field of Search .............. 536/23, 29; 424/180; 435/184

[56] References Cited

U.S. PATENT DOCUMENTS 3,462,416 8/1969 Hanze et al. ................ 536/26
4,163,839 8/1979 Umezawa et al. ............ 536/24

*Primary Examiner*—Johnnie R. Brown
*Assistant Examiner*—Blondel Hazel
*Attorney, Agent, or Firm*—John S. Roberts, Jr.

[57] ABSTRACT

Seven-membered heterocyclic nucleosides used to inhibit the deamination enzyme responsible for the inactivation of arabinosylcytosine (ara—C). Preferred nucleosides containing a seven-member aglycone are as follows:

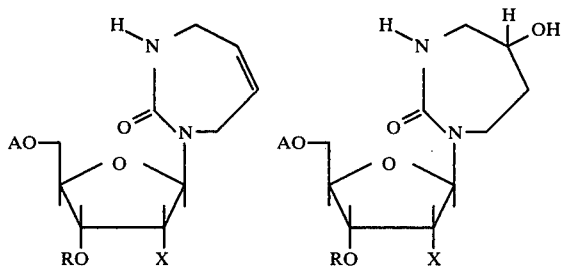

4     6

R = H, benzoyl, para-nitrobenzoyl
X = H, OR
A = R, mono-, di- and tri-phosphates ($PO_3E_2$, $P_2O_6E_3$, $P_3O_9E_4$)
E = H, Na Preferred aglycones are as follows:

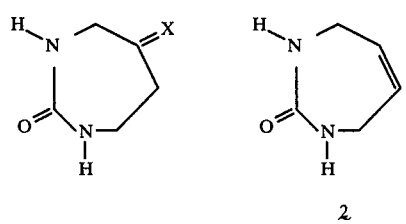

2

1a: X = $OCH_2CH_2O$
1b: X = $SCH_2CH_2S$
1c: X = O
1d: X = H, OH
1e: X = 2H

Active components utilized against pyrimidine deaminases from mammalian tissues (mouse kidney and human liver) showed optimum advantage when compared with tetrahydrouridine (THU).

7 Claims, No Drawings

SEVEN-MEMBERED RING COMPOUNDS AS INHIBITORS OF CYTIDINE DEAMINASE

This invention is directed to seven-member heterocyclic nucleosides and component aglycones used to inhibit the deamination enzyme responsible for inactivating arabinosylcytosine (ara-C). Preferred nucleosides containing an active seven-member ring are as follows:

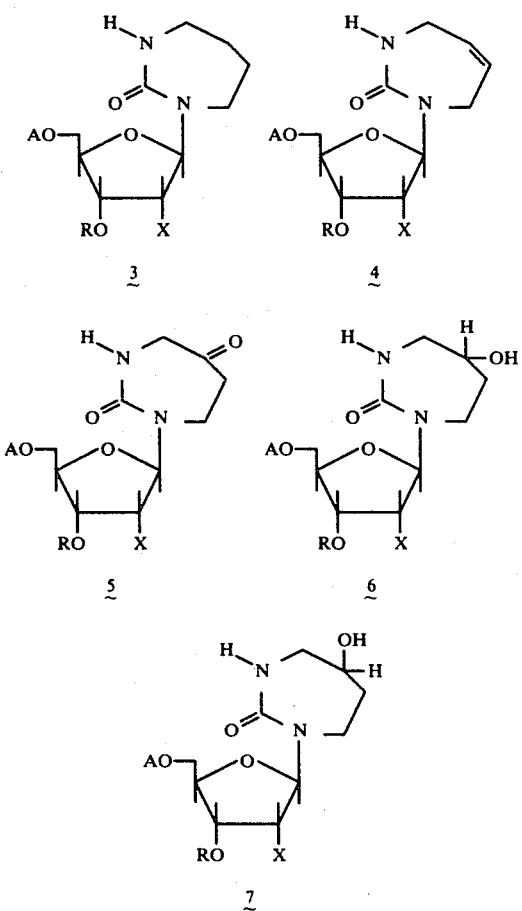

R = H, benzoyl, para-nitrobenzoyl
X = H, OR
A = R, mono-, di- and tri- phosphates ($PO_3E_2$, $P_2O_6E_3$, $P_3O_9E_4$)
E = H, Na Preferred aglycones are as follows:

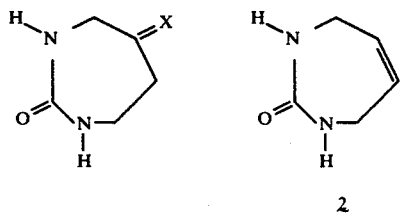

1a: X = OCH₂CH₂O
1b: X = SCH₂CH₂S
1c: X = O
1d: X = H, OH
1e: X = 2H

Active components utilized against pyrimidine deaminases from mammalian tissues (mouse kidney and human liver) showed optimum advantage when compared with tetrahydrouridine (THU).

PRIOR ART STATEMENT

U.S. Pat. No. 4,163,839 Umezawa et al treats coformycin and its inhibition of adenosine deaminase.

U.S. Pat. No. 3,462,416 Hanze treats tetrahydrouridine as a cytidine deaminase inhibitor.

Marquez et al, "Synthesis of 1,3-Diazepin-2-one Nucleosides as Transition-State Inhibitors of Cytidine Deaminase," submitted to the *Journal of the American Chemical Society*, adds the inhibition of the enzyme cytidine deaminase by the present compounds as compared to the relative action of THU.

PROTECTION OF AMINOPYRIMIDINE NUCLEOSIDES

Enzymes which deaminate natural aminopurine and aminopyrimidine nucleosides can also convert active drugs into inactive compounds in the human body. For example, the purine nucleoside arabinosyladenine (ara-A) shows little activity against standard animal tumors which are used as models for human cancer. This is because the enzyme adenosine deaminase converts the amino group of the drug rapidly to a hydroxyl group producing an inactive compound. When a potent inhibitor of this enzyme is co-administered with ara-A, excellent anti-tumor activity is observed. An excellent class of purine deaminase inhibitors, the coformycins, is known and these compounds have clinical activity.

Arabinosylcytosine (ara-C) is a pyrimidine nucleoside with excellent human anticancer properties in leukemias. Ara-C is degraded by cytidine deaminase to inactive arabinosyluracil. A potent inhibitor of cytidine deaminase will make ara-C an even more useful drug. The invention described herein describes a new class of very potent inhibitors of cytidine deaminase.

Inhibition of adenosine deaminase by the fermentation product coformycin (or 2'-deoxycoformycin) and of cytidine deaminase by tetrahydrouridine (THU) is believed to result from the similarity between these stable compounds and the respective tetrahedral substrate intermediates formed in the course of the enzymatic deamination reaction. These compounds are probably the best examples of the transition-state concept. While $K_m$ values for these two enzymes and their respective substrates differ only by about an order of magnitude depending on the enzyme source, coformycin and its 2'-deoxy analogue are far more potent in inhibiting adenosine deaminase than THU is in inhibiting cytidine deaminase. The purine deaminase inhibitors ($K_i$ $10^{-11}$ to $10^{-12}$ M) are roughly $10^4$ to $10^5$ times more tightly bound to its enzyme than THU is to cytidine deaminase ($K_i$ ca. $10^{-7}$ M). Two unique features appear in the structure of the aglycones of the potent purine deaminase inhibitors: an expanded seven-member ring and a hydroxyl group located two carbons away from a neighboring nitrogen atom in this ring. It was therefore of interest to determine if similar changes in the pyrimidine nucleus could result in compounds with affinities for cytidine deaminase approaching the values observed for the coformycins with adenosine deaminase. This invention describes the synthesis and enzyme inhibition activity of new, seven-member, pyrimidine-like nucleosides.

The plan to prepare nucleosides of the type 3-7 involved first the synthesis of the seven-member ring heterocycle and second its condensation with an appropriate sugar derivative. Methods were devised for the synthesis of the required heterocycles and their corresponding nucleosides which successfully afforded the desired compounds.

In general, for the ribosides containing an acyl protecting functionality, formation of the β-anomer is exclusive or predominant. This fact is probably due to the participation of the 2'-acyl function during the condensation reaction [Watanabe et al., *J. Carbohydr., Nucleosides, Nucleotides*, 1, 1 (1974)]. All the ribofuranosyl nucleosides isolated by this invention corresponded to the β-configuration, a fact that was consistent with the NMR spectral properties and biological activity of these nucleosides. In the 2'-deoxyribosyl series, however, the absence of the 2'-acyl protective group results in the formation of both α- and β-anomers which are separable by chromatography (Example 18).

ENZYME INHIBITION

The novel compounds described herein are potent inhibitors of cytidine deaminase. Indeed, 4b and 6b (see Examples 10 and 16, respectively) are the most potent known inhibitors of this enzyme (see Table 1 below).

TABLE 1

| Cytidine Deaminase Inhiibition | | |
|---|---|---|
| | $K_i$ (M) | |
| Compound | Mouse Kidney | Human Liver |
| Tetrahydrouridine (THU) | $2.2 \times 10^{-7}$ | $1 \times 10^{-7}$ |
| 5b (Example 12) | $2 \times 10^{-5}$ | $9 \times 10^{-6}$ |
| 8b (Example 14) | $1 \times 10^{-5}$ | $1 \times 10^{-5}$ |
| 3b (Example 8) | $3 \times 10^{-7}$ | $4 \times 10^{-7}$ |
| 3d (Example 19) | $2 \times 10^{-7}$ | — |
| 7b (Example 17) (mp 162°-164° C.) | $4 \times 10^{-7}$ | $9 \times 10^{-7}$ |
| 6b (Example 16) (mp 110°-112° C.) | $2 \times 10^{-8}$ | $4 \times 10^{-8}$ |
| 4b (Example 10) | $7 \times 10^{-8}$ | $2.5 \times 10^{-8}$ |

Based on molecular mechanistic considerations, it is quite possible that cytidine deaminase catalyzes the displacement of ammonia by water through an addition-elimination mechanism analogous to that proposed for adenosine deaminase. However, 2'-deoxycoformycin, the very potent adenosine deaminase inhibitor, has no significant activity against cytidine deaminase. The fact that 6b, designed as a coformycin analogue in the pyrimidine series, is the most potent known inhibitor of cytidine deaminase (ten times more potent than THU) tends to support the idea of an intrinsic mechanistic similarity between these two important deaminases.

The $K_i$ value for tetrahydro-2-oxopyrimidine riboside, the six-member ring aglycone analogue of 3b is $4 \times 10^{-6}$ M for the mouse kidney enzyme. Compound 3b is more than ten times more tightly bound to the enzyme (see Table 1) reflecting a potency increase of more than an order of magnitude in going from a six- to a seven-member ring aglycone. Placement of a hydroxyl group in the seven-member ring with the correct stereo-chemistry at carbon-5 (6b versus 3b) is responsible for another order of magnitude increase in binding to the enzyme. The precursor keto compound 5b behaved as a poor inhibitor of the enzyme.

With respect to the enzyme's specificity and the anomeric configuration of the glycosidic bond, the enzymatic assay proves to be a useful tool for assigning the β-configuration to the inhibitors prepared in the ribofuranosyl series. In addition to the chemical and spectral evidence, the enzyme's selectivity for the β-anomers constitutes additional proof for the β-configuration assigned to these nucleosides. Only β-cytidine, the natural substrate, is deaminated. α-cytidine, with the opposite configuration, was neither a substrate nor an inhibitor. This indicates that only nucleosides with the β-configuration fit into the enzyme's receptor site.

These potent inhibitors of cytidine deaminase could increase the efficacy and therapeutic usefulness of cytosine arabinoside (ara-C) in cancer treatment. The combination of these inhibitors with cytidine analogs (e.g., ara-C) and the study of the biological consequences of total depletion of cytidine deaminase activity constitute fruitful areas for additional antitumor drug research.

EXAMPLE 1

5-Ethylenedioxy-perhydro-1,3-diazepin-2-one (1a)

Step 1

A solution of 4.00 g (21 mmol) of 3-ketohexanedioic acid dimethyl ester [B. J. Whitlock and H. W. Whitlock, *J. Org. Chem.*, 39:3144 (1974)] in 100 mL of benzene was refluxed in the presence of 14.5 g (230 mmol) of ethylene glycol and 100 mg of p-toluene-sulfonic acid while water was azeotropically removed in a Dean-Stark trap. After 2.5 h, the mixture was cooled and washed with equal volumes of saturated sodium bicarbonate solution and water. The benzene layer was dried (MgSO$_4$) and reduced to dryness to leave a clear oil; IR (neat) 1740 cm$^{-1}$, NMR (CDCl$_3$) δ2.30 (A$_2$B$_2$ multiplet, 4), 2.60 (s,2), 3.65 (s,6), and 3.95 (s,4). The oily ketal was immediately hydrolyzed under reflux for 1.5 h in a solution of 4.4 g of 86% KOH in 50 mL of 95% ethanol. After cooling, the slight precipitate formed was dissolved by adding a small amount of water. Sufficient cation exchange resin AG50W-X8 (H+) was added to neutralize the base (pH ~6.5) and removal of the resin afforded a filtrate which was reduced to dryness to leave 4.3 g (99%) of 3-ketohexanedioic acid ethylene ketal as a yellowish oil which yielded a very hygroscopic solid after trituration with acetone; IR 1720 cm$^{-1}$ (broad); NMR δ(D$_2$O) 2.20 (A$_2$B$_2$ multiplet, 4), 2.60 (s,2), and 4.0 (s,4). This compound was not further characterized and used as such in the following step.

Step 2

3-Keto-hexanedioic acid ethylene ketal (4.30 g, 21 mmol) was dissolved in 10 mL of water and 27 mL of acetone. The solution was cooled to 0° C., 7 mL (50 mmol) of triethylamine in 35 mL of acetone was added and the solution cooled again to 0° C. Ethyl chloroformate (5.3 mL, 55 mmol) dissolved in 12 mL of acetone was added dropwise while maintaining the temperature at 0° C. Stirring was continued for 0.5 h at 0° C. followed by the slow addition of 4.27 g (66 mmol) of sodium azide dissolved in 20 mL of water. After the addition, the reaction mixture was stirred at 0° C. for 1 h. Immediately after, 75 mL of water was added and the reaction mixture extracted with 4×50 mL portions of ethyl acetate. The combined organic extracts were dried (MgSO$_4$) and reduced to dryness to leave a residual oil with the characteristic IR band at 2150 cm$^{-1}$. The oil was dissolved in 150 mL of benzene and refluxed for 1 h. Evaporation of the solvent yielded the bis-isocyanate as an oil which showed an intense IR band at 2260 cm$^{-1}$. This oil was mixed and stirred with 400 mL of a 4:1 acetone-water mixture for 14 h. Evaporation of the solvent produced the product as a solid residue which was triturated with acetone. The white solid obtained weighed 0.86 g (23.5%) and it was recrystallized from acetone; mp 193°-194°; IR 3250 and 1680 cm$^{-1}$; NMR (D$_2$O) δ2.10 (m,2), 3.20 (m,2), 3.25 (s,2), and 4.00 (s,4); mass spectrum m/e 172 (M.$^+$).

Anal. Calcd for C$_7$H$_{12}$N$_2$O$_3$: C, 48.82; H, 7.03; N, 16.27. Found: C, 48.78; H, 7.12; N, 16.10.

EXAMPLE 2

5-Ethylenedithio-perhydro-1,3-diazepin-2,5-dione (1b)

Step 1

A mixture of 15.00 g (79 mmol) of 3-ketohexanedioic acid dimethyl ester and 9 mL (107 mmol) of ethylene dithiol was treated at room temperature with 21 mL of boron trifluoride etherate. The reaction mixture was stirred for 0.5 h and then it was extracted with a mixture of benzene and saturated aqueous NaHCO$_3$. The benzene layer was washed further with NaHCO$_3$ and then dried (MgSO$_4$) and reduced to dryness to leave the thioketal a yellow oil; IR (neat) 1740 cm$^{-1}$. The oily thioketal was immediately hydrolyzed with 86% KOH in 95% ethanol. The reaction mixture was reduced to dryness and 200 mL of 50% aqueous acetone was added. Sufficient cation exchange resin (H+) was added to reach neutrality and extra amounts of acetone were required to keep the resulting acid in solution. The resin was removed and the aqueous acetone solution reduced to dryness to yield a white solid which was recrystallized from ethyl acetate to afford two crops totaling 11 g (58%) of 3-ketohexanedioic acid ethylene thioketal, mp 178°-80°; IR 1695 cm$^{-1}$, NMR (Me$_2$SO-d$_6$) δ2.35 (m,2), 2.65 (m,2), 2.95 (s,2), and 3.20 (s,4).

Anal. Calcd for C$_{18}$H$_{12}$O$_4$S$_2$: C, 40.65; H, 5.12; S, 27.14. Found: C,40.88; H, 5.30; S, 26.74.

Step 2

3-Ketohexanedioic acid ethylene thioketal (1.13 g, 4.78 mmol) was dissolved in 30 mL of acetone and cooled to 0° C. N,N-diisopropylethylamine (1.95 mL, 11.2 mmol) in 5 mL of acetone was added and the mixture was again cooled to 0° C. Ethyl chloroformate (1.51 mL, 15.83 mmol) in 2 mL of acetone was added dropwise while maintaining the temperature at 0° C. and the mixture was stirred further at that temperature for 0.5 h. Dropwise addition of 1.00 g (15.4 mmol) of sodium azide dissolved in 10 mL of water followed and the mixture was then stirred for 1 h at 0° C. Following a workup similar to that for Compound 1a (Example 1), the ethyl acetate extract was dried (MgSO$_4$) and reduced to dryness to leave the diacylazide as an oil with the characteristic 2150 cm$^{-1}$ IR band. The oil was rearranged to the bis-isocyanate in benzene to yield an oil with an intense isocyanate band at 2260 cm$^{-1}$. The rest of the reaction proceeded as for Compound 1a and 1.13 g (52%) yield of Compound 1b was obtained as a white solid. The material was recrystallized from acetone to yield Compound 1b as a crystalline white solid, mp 192°; IR 3200, 3050, and 1680 cm$^{-1}$; NMR (Me$_2$SO-d$_6$-D$_2$O) δ2.1 (m,2), 3.0 (m,2), 3.25 (s,4), and 3.60 (s,2); mass spectrum m/e 204 (M.$^+$).

Anal. Calcd for C$_7$H$_{12}$N$_2$OS$_2$: C, 41.15; H, 5.92; N, 13.71. Found: C, 41.33; H, 6.06; N, 13.34.

EXAMPLE 3

Perhydro-1,3-diazepin-2,5-dione (1c)

A suspension of 2.80 g (13.7 mmol) of Compound 1b in 80 mL of water was finely dispersed and magnetically stirred while 9.0 g (28 mmol) of mercuric acetate dissolved in 60 mL of water was added in one portion. Stirring continued for 14 h. Hydrogen sulfide gas was passed through the suspension for 15 minutes and all the insoluble materials were removed by filtration. The clear solution obtained was lyophilized to give a tan solid which was recrystallized twice from acetone (charcoal) to yield 0.580 g (35%) of Compound 1c as white needles, mp 158°-160° dec.; IR 3330, 1720, 1660, and 1620 cm$^{-1}$; mass spectrum m/e (rel. intensity) 128 (M$^+$·,21), 100 (15), 57 (6), 56 (7), 55 (5), 43 (8), 30 (100), 29 (15).

Anal. Calcd for C$_5$H$_8$N$_2$O$_2$: C, 46.86; H, 6.29; N, 21.86. Found: C, 46.57; H, 6.53; N, 21.60.

EXAMPLE 4

1,3,4,7-Tetrahydro-2H-1,3-diazepin-2-one (2)

To a solution of 0.5 g (5.8 mmol) of cis-1,4-diamino-2-butene [A. Feigenbaum and J. M. Lehn, *Bull. Soc. Chim. Fr.*, 198 (1973)] in 14 ml of 50% aqueous ethanol, carbonyl sulfide was infused with stirring over a period of 80-90 min. The salt formed in the reaction began to precipitate after 5-10 min. The reaction mixture was then heated to 70° C. and 0.7 mL of 1 N HCl was added. Heating at 70° C. was continued overnight and then the mixture evaporated to dryness in vacuo. The residue was extracted with methanol and the extract was chromatographed on a preparative TLC plate (Analtech silica gel GF, 2000μ) with CH$_2$Cl$_2$:MeOH (93:7). The desired product (Rf=0.44) was isolated as colorless crystals after recrystallization from methanol yielding 0.35 g (53%) of Compound 2, mp 182°-184°; IR (KBr) 3200 and 1660 cm$^{-1}$; NMR (CDCl$_3$—CD$_3$OD) δ3.68 (d, J=3 Hz, 4), 3.82 (s,2), and 5.83 (t, J=3 Hz, 2); mass spectrum m/e (rel. intensity) 112 (M$^+$·,19), 111 (25), 97 (68), 69 (42), 68 (61), 56 (69), 41 (58), 30 (50), 28 (100).

Anal. Calcd for C$_5$H$_8$N$_2$O: C, 53.56; H, 7.19; N, 24.98. Found: C, 53.42; H, 7.04; N, 24.75.

EXAMPLE 5

(±)-5-Hydroxy-perhydro-1,3-diazepin-2-one (1d)

Method A,

A solution of 0.10 g (0.78 mmol) of Compound 1c (Example 3) in 10 mL of water was stirred for 2 h in the presence of 0.10 g (2.6 mmol) of NaBH$_4$. After treating the solution with a strong cation exchange resin (H+), the filtrate was reduced to dryness. The residue was dissolved in methanol and reduced again to dryness. This process was repeated three times. Finally, the clear oily residue solidfied on standing to give Compound 1d quantitatively as a white solid. This solid was recrystallized from acetone to give pure 1d, mp 133°-34°; IR (KBr) 3250 and 1650 cm$^{-1}$; NMR (D$_2$O) δ1.90 (m,2), 3.20 (t, J=7 Hz, 2), 3.20 (d, J=7 Hz, 2), and 4.0 (m,l); mass spectrum m/e (rel. intensity) 130 (M$^+$·,20), 112 (4), 101 (15), 87 (42), 72 (13), 57 (37), 30 (100).

Anal. Calcd for C$_5$H$_{10}$N$_2$O$_2$: C, 46.14; H, 7.74; N, 21.53. Found: C, 45.96; H, 7.90; N, 21.28.

Method B.

To 0.078 g (0.7 mmole) of Compound 2 (Example 4) placed in a dry three-necked flask under nitrogen and cooled to 0° C., 2 mL (2 mmole) of a 4° C. solution of 1 M BH$_3$.THF was added through a septum cap. The mixture was stirred for 15 min. at 0° C. and allowed to warm up to room temperature. A colorless gel was formed. After sitting for 2.5 h, 1 mL of water was added followed by the dropwise addition of 3 mL of aqueous 1 N NaOH and 3 mL of 30% H$_2$O$_2$. The reaction mixture was stirred at room temperature for 1 h, reduced to dryness and co-evaporated several times with methanol. The residue was extracted with methanol and purified on a preparative silica gel TLC plate with CH$_2$Cl$_2$—MeOH (4:1) to afford 0.073 g (80%) of Compound 1d (Rf=0.39) as a crystalline material identical in all respects to the compound obtained through Method A.

EXAMPLE 6

Perhydro-1,3-diazepin-2-one (1e)

A solution of Compound 2 (Example 4) (0.050 g, 0.446 mmole) in 10 mL of methanol was hydrogenated at 35 psi for 9 hr in the presence of 20 mg of 10% Pd/C. The catalyst was removed and the filtrate reduced to dryness to provide colorless crystals (mp 166°–170°) of the known compound 1e [H. Ulrich, B. Tucker, and R. Richter, *J. Org. Chem.*, 43:1544 (1978)].

EXAMPLE 7

1-(2,3,5-Tribenzoyl-β-D-ribofuranosyl)-perhydro-1,3-diazepin-2-one (3a; X=OR, R=A=COC$_6$H$_5$)

A suspension of Compound 1e (Example 6) (2.00 g, 17.5 mmol), which was prepared according to the procedure of Ulrich et al., *J. Org. Chem.*, 43:1544 (1978) was stirred in 40 mL of dry acetonitrile at room temperature under anhydrous conditions. A solution (30 mL) of bis-(trimethylsilyl)-trifluoroacetamide (BSTFA) was added and stirred for 2 h. at room temperature. The excess reagents were removed in vacuo to leave an oil which was dissolved in 60 mL of dry benzene and added to a mixture of HgO (6.58 g) and HgBr$_2$ (6.58 g) heated under reflux in 240 mL of benzene. After 10 min., a solution of 2,3,5-tribenzoyl-D-ribofuranosyl bromide [prepared from 11.06 g (21.9 mmol) of 2,3,5-tribenzoyl-β-D-ribofuranosyl acetate according to Stevens et al., *J. Org. Chem.*, 33:1806 (1968)] in 40 mL of benzene was added. The whole mixture was stirred and heated under reflux for 15 h. After cooling, the mixture was filtered through a bed of Celite and the filter cake washed with ethyl acetate. The combined filtrate and washings were washed with saturated sodium bicarbonate and water and dried over MgSO$_4$. The organic extract was concentrated to 3–4 mL and applied to a dry column (Silica Woelm TSC, ICN) and eluted with 3:2 ethyl acetate-hexane (v/v). The desired nucleoside was isolated as a dry foam (4.49 g, 46%) after evaporation of the solvent (Rf=0.51, 3:2 ethyl acetate-hexane), mp 59°–61° C.; NMR (CDCl$_3$) δ 1.1–1.8 (br s, 4), 2.8–3.4 (br m, 4), 4.57 (m, 3), 5.27 (m, 1), 5.70 (m, 2), 6.12 (m, 1, H'$_1$), 7.0–8.1 (2m, 15).

Anal. Calcd for C$_{31}$H$_{30}$N$_2$O$_8$: C, 66.66; H, 5.41; N, 5.01. Found: C, 66.96; H, 5.37; N, 5.04.

EXAMPLE 8

1-(β-D-Ribofuranosyl)-perhydro-1,3-diazepin-2-one (3b; X=OH, R=A=H)

A solution of 0.9 g (1.61 mmol) of the protected nucleoside (3a; Example 7) in 3–4 mL of methanol was added to 100 mL of a saturated methanolic ammonia solution and kept in a pressure bottle at room temperature for 20 h. The solution was reduced to dryness and extracted with CHCl$_3$ and water. The aqueous layer was washed several times with CHCl$_3$ and lyophilized. The lyophilized material (323 mg, 82%) was recrystallized from a mixture of MeOH—CHCl$_3$—Et$_2$O to give colorless crystals, mp 165°–166° C.; NMR (D$_2$O—TSP) δ 1.6–1.8 (br s, 4), 3.0–3.4 (br m, 4) 3.6–4.2 (br m, 5), 5.38 (multiplet, 1, H'$_1$); [α]$_D^{25}$= −138° (c, 0.1 H$_2$O).

Anal. Calcd for C$_{10}$H$_{18}$N$_2$O$_5$: C, 48.77; H, 7.37; N, 11.38. Found: C, 48.44; H, 7.63; N, 11.29.

EXAMPLE 9

1-(2,3,5-Tribenzoyl-β-D-ribofuranosyl)-1,3,4,7-tetrahydro-2H-1,3-diazepin-2-one (4a; X=OR, R=A=COC$_6$H$_5$)

A suspension of Compound 2 (Example 4) (560 mg, 5 mmol) was stirred in 25 mL of dry acetonitrile at room temperature under anhydrous conditions. A solution (19 mL) of bis-(trimethylsilyl)-trifluoroacetamide (BSTFA) was added and stirred for 2 h. at room temperature. The excess reagents were removed in vacuo to leave an oil which was dissolved in 20 mL of dry benzene and added to a mixture of HgO (1.88 g) and HgBr$_2$ (1.88 g) heated under reflux in 80 mL of benzene. After 10 min., a solution of 2,3,5-tribenzoyl-D-ribofuranosyl bromide [prepared from 3.16 g (6.26 mmol) of 2,3,5-tribenzoyl-β-D-ribofuranosyl acetate according to Stevens et al., *J. Org. Chem.*, 33:1806 (1968)] in 20 mL of benzene was added. The whole mixture was stirred and heated under reflux for 15 h. After similar work-up as before, the organic extract was concentrated to 3–4 mL and applied to a dry column (Silica Woelm TSC, ICN) and eluted with 2:3 ethyl acetate-hexane (v/v). The desired nucleoside was isolated as a dry foam (1.43 g, 51%) after evaporation of the solvent (Rf=0.19, 2:3 ethyl acetatehexane), mp 63°–4° C.; NMR (CDCl$_3$) 3.6–3.8 (m,4), 4.60 (m,3), 5.10 (m,1), 5.60 (m,2), 5.70 (m,2), 6.06 (d,1,J=6 Hz,H'$_1$), 7.0–8.2 (2m,15).

Anal. Calcd for C$_{31}$H$_{28}$N$_2$O$_8$·0.35 H$_2$O: C, 66.15; H, 5.14, N, 4.98; H$_2$O, 1.12. Found: C, 66.05; H, 5.33; N, 4.76; H$_2$O, 1.15 (Karl Fischer).

EXAMPLE 10

1-(β-D-Ribofuranosyl)1,3,4,7-tetrahydro-2H-1,3-diazepin-2-one (4b; X=OH, R=A=H)

Under the same experimental conditions as used for the preparation of Compound 3b (Example 8) this compound was obtained in 92% yield as the lyophilized powder, mp 132°–135° C.; NMR (CD$_3$OD—D$_2$O) δ 3.6–3.9 (m,7), 3.9–4.1 (m,2), 5.47 (m,6 Hz wide,1,H'$_1$), 5.83 (t,2,J=3 Hz).

EXAMPLE 11

1-(2,3,5-Tribenzoyl-β-D-ribofuranosyl)-5-keto-perhydro-1,3-diazepin-2-one (5a; X=OR, R=A=COC$_6$H$_5$)

Heterocycle (1c) (Example 3) (0.642 g, 5 mmol) was suspended in 25 mL of dry acetonitrile and treated with excess of bis-(trimethylsilyl)-trifluoroacetamide (BSTFA, 20 mL) and stirred at room temperature for 2h. The solvent and excess reagent were removed in vacuo under careful anhydrous conditions. The residual persilylated heterocycle was dissolved in dry benzene (10 mL) and added immediately to a refluxing mixture of 1.8 g each of HgO and HgBr$_2$ in 60 mL of benzene. Immediately after, 2,3,5-tribenzoyl-D-ribofuranosyl bromide, prepared from 3.16 g (6.26 mmol) of 2,3,5-tribenzoyl-β-D-ribofuranosyl acetate, according to Stevens et al, *J. Org. Chem.*, 33:1806 (1968), was added as a benzene solution in 20 mL of solvent. The refluxing continued for 16 h. After cooling, the catalyst was removed by filtration and the benzene solution was extracted twice with concentrated NaHCO$_3$ solution. The organic extract was dried (MgSO$_4$) and reduced to dryness to yield a foamy residue. Silica gel thin layer chromatography (TLC) in ethyl acetate-hexane (3:1) revealed presence of two components with Rf values of 0.28 and 0.65, respectively. The high Rf component was eliminated by dry column chromatography using silia gel and ethyl acetate. This component proved to be an unwanted sugar decomposition product. The low Rf component was further purified from minor contaminants by regular column chromatography using silica gel and ethyl acetate-hexane (3:1) providing 1.3 g (45.3%) of Compound 5a as a foam, mp 65°–75° C.; NMR (CDCl$_3$) δ 2.6 (m,2), 3.7 (m,4), 4.6 (m,3), 5.8 (m,2), 6.3 (m,2), 7.4 (m,10), and 8.0 (m,5). After D$_2$O exchange the signal at δ 6.3 became a simplified multiplet integrating for just one proton (C'$_1$ proton) and the multiplet at δ 3.7 simplified to an AB quartet (J = 14 Hz) for the geminal protons at C4 and a multiplet for the protons at C7. Mass spectrum m/e 572 (M$^+$·).

EXAMPLE 12

1-(β-D-Ribofuranosyl)-5-keto-perhydro-1,3-diazepin-2-one (5b; X=OH, R=A=H)

Under the same experimental conditions used for the preparation of Compound 3b (Example 8), this compound was obtained in 80% yield. Purification of the product by preparative TLC [silica gel, CH$_2$Cl$_2$: MeOH (7:3)] gave pure (Rf=0.28) product which was later obtained as a lyophilized powder, mp 85°–90°; NMR (D$_2$O) δ2.0 (t,J=5 Hz,2), 3.2(m,4), 3.4–4.2 (m,5), 5.35 (d,l,J=7 Hz,H'$_1$).

EXAMPLE 13

3-(2,3,5-Tribenzoyl-β-D-ribofuranosyl)-5-keto-perhydro-1,3-diazepin-2-one (8a; A=2H, B=O, X=OR, R=D=COC$_6$H$_5$)

Under the same experimental conditions as above, this isomer of Compound 5a (Example 11) was obtained along with 5a when the persylylated (1c; Example 3) was refluxed with the mercury catalysts for about ten minutes prior to the addition of the bromosugar. Under these conditions, 8a was the major component of the mixture and it appeared on TLC with an Rf value of 0.18. Separation was accomplished by a similar procedure as above affording the pure isomer in 37.5% as a thick syrup. NMR (CDCl$_3$) δ2.8 (m,2), 3.35 (m,2), 3.95 (s,2), 4.6 (m,3), 5.6 (m,3), 6.1 (d,l,J=6 Hz), 7.4 (m,10) and 8.0 (m,5); mass spectrum m/e 572 (M$^+$·).

EXAMPLE 14

3-(β-D-Ribofuranosyl)-5-keto-perhydro-1,3-diazepin-2-one (8b; A=2H, B=O, X=OR, R=D=H)

Under identical experimental conditions as for Compounds 3b (Example 8) and 5b (Example 12), this material was isolated pure as a lyophilized hygroscopic powder, NMR (D$_2$O) δ2.0 (m,2), 2.9–3.4 (m,4), 3.4–4.4 (m,5), 5.4 (d,l,J=6 Hz,H'$_1$).

EXAMPLE 15

1-(2,3,5-Tribenzoyl-β-D-ribofuranosyl)-5-hydroxyperhydro-1,3-diazepin-2-one; Diastereomers 6a and 7a (X=OR; R=A=COC$_6$H$_5$)

To a solution of Compound 5a (Example 11) (0.750 g, 1.31 mmol) in tetrahydrofuran (30 mL) containing 10 drops of water was added 0.075 g (1.98 mmol) of sodium borohydride. The reaction mixture was held at room temperature under stirring for 1.5 h. Methanol (5 mL) and cation exchange resin Bio-Rad AG-50W-X8 (H$^+$ form) was added to achieve neutrality. After filtration the filtrate was reduced to dryness to yield a syrupy oil which showed two clean spots on TLC (silica gel, ethyl acetate) with Rf values of 0.21 and 0.16, respectively. Using preparative TLC (2000µ thickness), under the same system, the components were separated after 4 consecutive developments giving 0.400 g and 0.300 g, of the high Rf (Compound 6a) and low Rf (Compound 7a) isomers, respectively.

Compound 6a, High Rf isomer; NMR (CDCl$_3$) δ1.7 (m,2), 2.3 (m,l, D$_2$O exchanged), 2.8–3.8 (m,5), 4.6 (m,3), 5.0 (m,l, D$_2$O exchanged), 5.7 (m,2), 6.0 (m,1), 7.4 (m,10), and 8.0 (m,5).

Compound 7a, Low Rf isomer; NMR (CDCl$_3$) δ1.6 (m,2), 2.5 (m,l, D$_2$O exchanged), 3.2 (m,4), 3.8 (m,l), 4.6 (m,3), 5.1 (m,l, D$_2$O exchanged), 5.6 (m,2), 6.0 (m,1), 7.4 (m,10), and 8.0 (m,5).

EXAMPLE 16

1-(β-D-Ribofuranosyl)-5-hydroxy-perhydro-1,3-diazepin-2-one (6b; X=OH, R=A=H); Single diastereomer from the high Rf isomer (6a)

A solution of 0.4 g of the high Rf isomer (6a) in a few mL of chloroform was added to 50 mL of a saturated methanolic ammonia solution and kept in a pressure bottle at room temperature for 20 h. The solution was reduced to dryness and extracted with CHCl$_3$ and water. The aqueous layer was washed several times with CHCl$_3$ and then it was treated with charcoal, filtered, and lyophilized. The lyophilized material (0.160 g, 87%) was recrystallized from a mixture of MeOH—CHCl$_3$—Et$_2$O to give white needles, mp 110°–112°; IR (KBr), 3250 and 1600 cm$^{-1}$, NMR (CD$_3$OD) δ5.4 (multiplet, 6 Hz wide, 1,H'$_1$); [α]$_D^{25}$ −115° (C 0.1, H$_2$O).

Anal. Calcd for C$_{10}$H$_{18}$N$_2$O$_6$.0.5H$_2$O: C, 44.27; H, 7.06; N, 10.33; O, 38.33. Found: C, 44.15; H, 7.19; N, 10.36; O, 38.14.

EXAMPLE 17

1-(β-D-Ribofuranosyl)-5-hydroxy-perhydro-1,3-diazepin-2-one (7b; X=OH, R=A=H); Single diastereomer from the low Rf isomer (7a)

Under the same experimental conditions, this compound was obtained in 80%. It was recrystallized from a similar mixture of solvents to afford 7b as white needles, mp 162°–164°; IR (KBr) 3250 and 1620 cm$^{-1}$, NMR (D$_2$O), δ5.40 (d,l,J=6 Hz,H'$_1$); [α]$_D^{25}$ −183° (C 0.1, H$_2$O).

Anal. Calcd for C$_{10}$H$_{18}$N$_2$O$_6$: C, 45.80; H, 6.90; N, 10.70; O, 36.60. Found: C, 45.76; H, 7.01; N, 10.64; O, 36.50.

EXAMPLE 18

1-[2-deoxy,3,5-di-O-(p-nitrobenzoyl)-D-erythro-pentofuranosyl]-perhydro-1,3-diazepin-2-one (α- and β-anomers of 3c, X=H, R=A=p-nitrobenzoyl)

A suspension of compound 1e (Example 6) (0.163 g, 1.43 mmol) was stirred in 10 mL of dry acetonitrile at room temperature under anhydrous conditions in the presence of 5 mL of BSTFA for 2 h. The excess of reagents were removed in vacuo to leave an oil which was dissolved in 10 mL of dry benzene and added to a mixture of HgO (0.536 g) and HgBr$_2$ (0.536 g) in 50 mL of refluxing benzene. Soon after, 0.8 g of 2-deoxy-3,5-di-O-(p-nitrobenzoyl)-D-erythropentosyl chloride [prepared according to R. K. Ness et al., *J. Org. Chem.*, 26:2895 (1961)] in 10 mL of methylene chloride was added. The entire mixture was refluxed for 2 h. After cooling and filtering through Celite, the benzene solution was extracted with saturated sodium bicarbonate solution and water and dried over MgSO₄. The organic extract was purified on a short silica gel column eluted first with benzene and then with ethyl acetate. This process removed unreacted sugar residues and the desired fractions contained only the two α- and β-anomers which were separable by fractional crystallization and chromatography (preparative tlc on silica gel with ethyl acetate).

High Rf anomer (Rf=0.39):

isolated in 30% yield as a crystalline solid, mp 130° C., NMR (CDCl₃) δ1.6 (br s,4), 2.3 (m,2), 3.1 (br s,4), 4.4 (m,1), 4.6 (m,2), 4.9 (br s,1,D₂O exchanged), 5.5 (m,1), 6.1 (t,1,J=8 Hz), 8.2 (s,8).

Low Rf anomer (Rf=0.31):

isolated in low yield (ca. 5%) as an oil, NMR (CDCl₃) 1.6 (br s,4), 2.2-2.8 (m,2), 3.1 (br s,2), 3.3 (br s,2), 4.5 (s,3), 5.1 (m,1, D₂O exchanged), 5.5 (m,1), 6.1 (t,1,J=7 Hz), 8.2 (s,8).

EXAMPLE 19

1-(2-deoxy-D-erythro-pentofuranosyl)-perhydro-1,3-diazepin-2-one (single anomer, 3d, X=H, R=A=H)

From the high Rf isomer of 3c (0.15 g, 2.83 mmol) (Example 18) deprotection with methanolic ammonia in the usual manner as in 3b (Example 8) afforded 8c as a foam in good yield, NMR (CD₃OD) δ1.7 (br s,4), 2.0 (m,2), 3.1 (br s,4), 3.6 (m,3), 4.2 (m,1), 5.95 (t,1,J=7 Hz).

EXAMPLE 20

Cytidine Deaminase Inhibition Assay Procedure

Mouse kidney cytidine deaminase was isolated and partially purified from mouse kidney acetone powder obtained from Sigma Chemical Co., St. Louis, Mo. 63178. The powder was extracted with pH 8.0 phosphate butter (0.05 M) and the extract filtered through a Nalgene filter unit (0.45 micron grid membrane) to yield a clear yellow filtrate. The filtrate was then fractionated with ammonium sulfate. The K_m for deamination of cytidine using this preparation was found to be 5×10⁻⁵ M, in agreement with the value of 7×10⁻⁵ M reported by Tomchick et al, *J. Biol. Chem.*, 243:2534 (1968) for mouse kidney cytidine deaminase.

Cytidine deaminase from human liver was isolated by the procedure of Wentworth et al, *Biochemistry*, 14:5099 (1975).

We claim:

1. Nucleoside compounds which are useful in the prevention of deaminating arabinosylcytosine (ara—C) selected from the group consisting of the following:

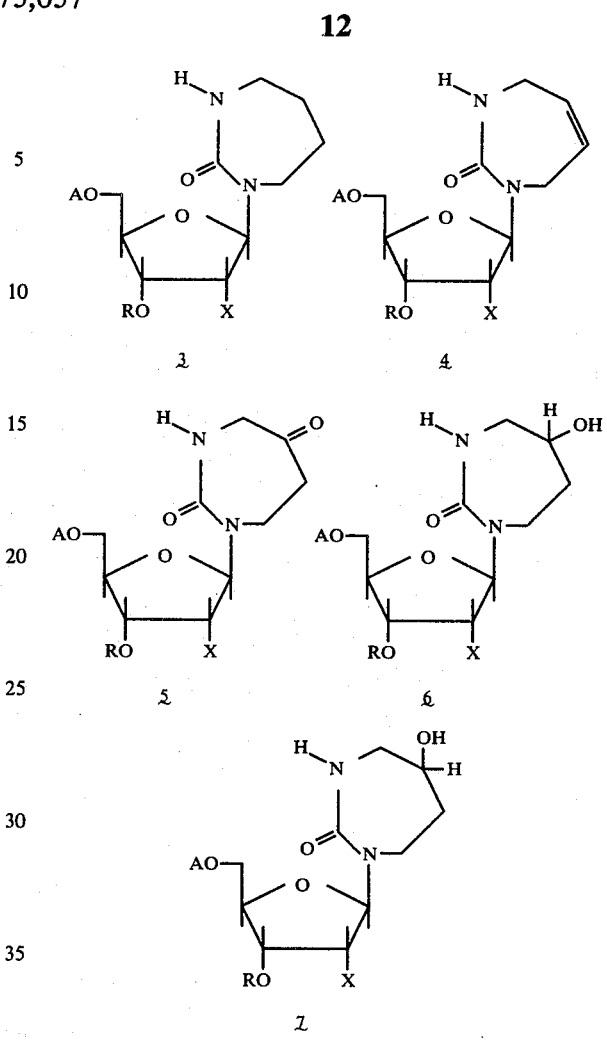

wherein R is selected from the group consisting of H, benzoyl, paranitrobenzoyl; X is selected from the group consisting of H, OR; A is selected from the group consisting of R, mono-, di- and tri-phosphates (PO₃E₂, P₂O₆E₃, P₃O₉E₄); and E is selected from the group consisting of H, Na.

2. The nucleoside according to claim 1 wherein the compound is Compound 4.

3. The nucleoside according to claim 1 wherein the compound is Compound 6.

4. The nucleoside according to claim 1 wherein the compound is Compound 7.

5. A method of inhibiting cytidine deaminase which comprises utilizing an effective amount of a glycoside selected from the following:

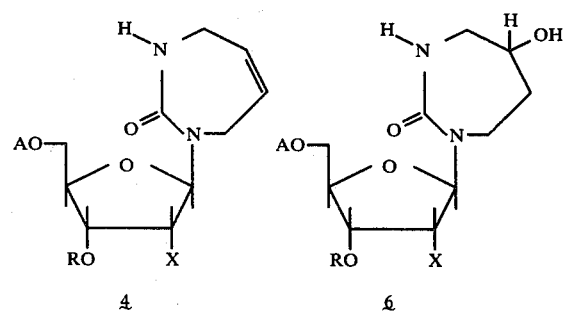

wherein R is selected from the group consisting of H, benzoyl, paranitrobenzoyl; X is selected from the group consisting of H, OR; A is selected from the group consisting of R, mono-, di- and tri-phosphates ($PO_3E_2$, $P_2O_6E_3$, $P_3O_9E_4$); and E is selected from the group consisting of H, Na.

6. The method according to claim 5 wherein the compound is Compound 4.

7. The method according to claim 5 wherein the compound is Compound 6.